United States Patent
Ishizuka et al.

(10) Patent No.: US 9,078,558 B2
(45) Date of Patent: Jul. 14, 2015

(54) HOLE INSPECTION METHOD AND HOLE INSPECTION DEVICE

(75) Inventors: Yasutaka Ishizuka, Tochigi (JP); Satoshi Oikawa, Tochigi (JP); Michiaki Ohkubo, Tochigi (JP); Masaichi Ohno, Tochigi (JP)

(73) Assignee: HONDA MOTOR CO., LTD., Tokyo (JP)

( * ) Notice: Subject to any disclaimer, the term of this patent is extended or adjusted under 35 U.S.C. 154(b) by 415 days.

(21) Appl. No.: 13/565,694

(22) Filed: Aug. 2, 2012

(65) Prior Publication Data

US 2013/0093876 A1 Apr. 18, 2013

(30) Foreign Application Priority Data

Oct. 13, 2011 (JP) ................................. 2011-225947

(51) Int. Cl.
*H04N 7/18* (2006.01)
*A61B 1/00* (2006.01)
*A61B 1/12* (2006.01)
*G02B 23/24* (2006.01)

(52) U.S. Cl.
CPC .................. *A61B 1/00* (2013.01); *A61B 1/0008* (2013.01); *A61B 1/00064* (2013.01); *A61B 1/00071* (2013.01); *A61B 1/00091* (2013.01); *A61B 1/12* (2013.01); *G02B 23/2492* (2013.01)

(58) Field of Classification Search
CPC ........... H04N 7/18; H04N 5/91; H04N 5/225; H04N 5/232; H04N 5/23222; H04N 9/045; H04N 2005/2255

USPC ................. 348/82, 84, 85; 73/152.58; 367/35
See application file for complete search history.

(56) References Cited

U.S. PATENT DOCUMENTS

| | | | |
|---|---|---|---|
| 4,883,355 A | 11/1989 | Saghatchi et al. | |
| 4,938,060 A * | 7/1990 | Sizer et al. ................. | 73/152.58 |
| 5,191,173 A * | 3/1993 | Sizer et al. ................. | 174/105 R |
| 2005/0281520 A1 | 12/2005 | Kehoskie et al. | |
| 2010/0317922 A1 | 12/2010 | Kumai | |

FOREIGN PATENT DOCUMENTS

| | | |
|---|---|---|
| EP | 0 242 428 A2 | 10/1987 |
| JP | 58-62612 A | 4/1983 |
| JP | 10-76825 A | 3/1989 |
| JP | 1-130119 A | 5/1989 |
| JP | 1-229218 A | 9/1989 |
| JP | 1-229219 A | 9/1989 |
| JP | 1-255821 A | 10/1989 |

(Continued)

*Primary Examiner* — Trang U Tran
(74) *Attorney, Agent, or Firm* — Rankin, Hill & Clark LLP (57) ABSTRACT

While an insert shaft (11) disposed with a wide angle lens (15) at a top end thereof is being inserted into a hole to inspect a wall surface of the hole on the basis of an image photographed through the wide angle lens (15), gas is injected into the innermost recess of the hole along the outer circumferential surface of the insert shaft (11) by a gas injection mechanism (19). The gas injection mechanism (19) is provided with a guide (13) configured to surround a top end portion of the insert shaft (11) and form a gas injection passage (R) extending in the longitudinal direction of the insert shaft (11) between the inner circumferential surface of the guide (13) and the outer circumferential surface of the insert shaft (11), and a gas supply unit (14c) configured to supply gas to an inner space of the guide (13).

9 Claims, 2 Drawing Sheets

(56) References Cited

FOREIGN PATENT DOCUMENTS

| JP | 6-98854 A | 4/1994 |
| JP | 08-050207 A | 2/1996 |
| JP | 9-43517 A | 2/1997 |
| JP | 2008-178511 A | 8/2008 |
| JP | 2009-39325 A | 2/2009 |
| JP | 2010-8551 A | 1/2010 |

* cited by examiner

HOLE INSPECTION METHOD AND HOLE INSPECTION DEVICE

TECHNICAL FIELD

The present invention relates to a hole inspection method and a hole inspection device.

BACKGROUND ART

Hitherto, an industrial endoscope has been used to image an inner side wall surface (hereinafter, referred to as a hole wall surface) of a hole-like inspection subject (hereinafter, referred to as an inspection hole) to inspect whether or not a defect is present on the hole wall surface. In order to conduct the inspection, an insert shaft which is long and thin and is disposed with a wide angle lens at the top end thereof is inserted into the inspection hole. In the inspection, if an adhered substance such as a water drop, a chip, a foreign substance or the like adheres to the lens or the hole wall surface, it is impossible to inspect accurately whether or not a defect or the like is present from a picture imaged by the endoscope.

Thereupon, there has been disclosed in Japanese Patent Laid-open No. H08-050207 a fiberscope attached with a cleaning mechanism which is configured to blow air to a top end surface of a fiber cable to clean a foreign substance adhered to the top end surface. In the fiberscope, a flexible pipe is disposed to cover the outer circumferential surface of the fiber cable so as to form an air passage between the inner circumferential surface of the flexible pipe and the outer circumferential surface of the fiber cable, and a top end portion of the flexible pipe is bent inward to form an air injection portion.

SUMMARY OF INVENTION

Problem to be solved by the invention

However, according to the art disclosed in Japanese Patent Laid-open No. H08-050207, even it is possible to clean the foreign substance adhered to the top end surface of the fiber cable, it is impossible to clean the adhered substance adhered to the hole wall surface. Therefore, the adhered substance adhered to the hole wall surface prevents the inspection from being conducted accurately.

Moreover, conventionally when a foreign substance in the inspection hole is confirmed by the fiber cable, a cleaning tool is inserted into the hole to clean the foreign substance. However, in the case of a thin hole, when the cleaning tool is inserted into the hole, a great load is acted on the fiber cable; therefore, it is undesirable. In the case of a thinner hole, the fiber cable has to be removed out of the hole so as to insert only the cleaning tool into the hole. Thereby, the cleaning tool has to be pressed to the cleaning position without the reference of an image; it would be very difficult to perform such operation.

The present invention has been accomplished in view of the aforementioned problems, and it is therefore an object of the present invention to provide a hole inspection method and a hole inspection device capable of easily cleaning an adhered substance adhered to a wall surface of a hole even though it is a thin hole.

Means for Solving the Problem

The present invention provides a hole inspection method for inspecting a wall surface of a hole wherein while an insert shaft disposed with a wide angle lens at a top end thereof is being inserted into the hole to inspect the wall surface of the hole on the basis of an image acquired through the wide angle lens, gas is injected into an innermost recess of the hole along an outer circumferential surface of the insert shaft.

According to the hole inspection method of the present invention, by injecting gas into the innermost recess of the hole along the outer circumferential surface of the insert shaft, it is possible to clean an adhered substance such as a water drop, a chip, a foreign substance or the like adhered to the wall surface of the hole. Further, it is also possible to clean the mist, the water drop or the like from the lens surface. Accordingly, it is possible to improve the inspection accuracy. In addition, the hole is such a hole disposed with, for example, a fuel injection device.

The present invention provides a hole inspection device for inspecting a wall surface of a hole, comprising: an insert shaft which is provided with a wide angle lens at a top end thereof and is configured to be inserted into the hole, and a gas injection mechanism configured to inject as into an innermost recess of the hole along an outer circumferential surface of the insert shaft.

According to the hole inspection device of the present invention, the gas injection mechanism injects gas into the innermost recess of the hole along the outer circumferential surface of the insert shaft. Thereby, it is possible to clean an adhered substance such as a water drop, a chip, a foreign substance or the like adhered to the lens or the wall surface of the hole, and it is also possible to clean the mist, the water drop or the like from the lens surface. Accordingly, it is possible to improve the inspection accuracy. In addition, the hole is such a hole disposed with, for example, a fuel injection device.

In the hole inspection device of the present invention, it is desirable that the gas injection mechanism is provided with a guide configured to surround a top end portion of the insert shaft and form a gas injection passage extending in the longitudinal direction of the inset shaft between the outer circumferential surface of the insert shaft, and a gas supply unit configured to supply gas to an inner space of the guide.

Herein, the top end portion of the insert shaft may be supported at the center of the inner space of the guide without contact by the gas pressure of the gas injection passage. Thereby, the top end portion of the insert shaft can be perfectly supported with the axial center thereof matched with the center of the inner space of the guide. Moreover, it is possible to make the top end side portion of the hole inspection device having the gas injection mechanism thin and simple in structure.

It is desirable that the hole inspection device of the present invention is further provided with a supporter having a gas chamber which is supplied with gas from the gas supply unit, houses a collar member disposed at a basal end of the guide, and communicates the inner space of the guide, wherein the insert shaft is configured to insert through the guide and the gas chamber in the longitudinal direction and a basal end portion thereof is supported by the supporter.

Herein, the basal end portion of the insert shaft is supported by the supporter and the top end portion thereof is supported by the gas pressure. Accordingly, it is possible to support the insert shaft stably at a high precision to prevent the position deviation of the top end portion. Thereby, there is no need to use a large-scale bush mechanism which is highly precise but expensive, which makes it possible to miniaturize the supporter and thereby lower the cost of the device.

Moreover, the collar member of the guide is pressed on the bottom surface of the gas chamber by the gas pressure, thereby, the guide moves only when an external force which is greater than the gas pressure is acted on the guide. Accordingly, even though the guide contacts the wall surface of the hole, the guide moves instantly; thereby, it is possible to inhibit the damage to the wall surface of the hole to the minimum.

DESCRIPTION OF EMBODIMENTS

A hole inspection device 10 according to an embodiment of the present invention will be described with reference to FIG. 1. The hole inspection device 10 is so used to inspect whether or not a defect such as a cavity or the like is present in an inner wall surface (hereinafter, referred to as a hole wall surface) of a hole-like inspection subject (hereinafter, referred to as an inspection hole).

The inspection hole refers to a hole formed to dispose, for example, a fuel injection device (injector) of a direct fuel-injection engine; however, the usage, the shape, the diameter, the depth or the like thereof is not limited. For example, it is acceptable that the inspection hole is a through hole or a hole having a bottom surface. Moreover, it is acceptable that the inspection hole is a straight hole having a constant hole diameter or a taper hole having a gradually varying hole diameter.

The hole inspection device 10 is provided with an insert shaft 11, a support bracket (supporter) 12, a guide 13 and a gas supply mechanism 14.

Figure 1:
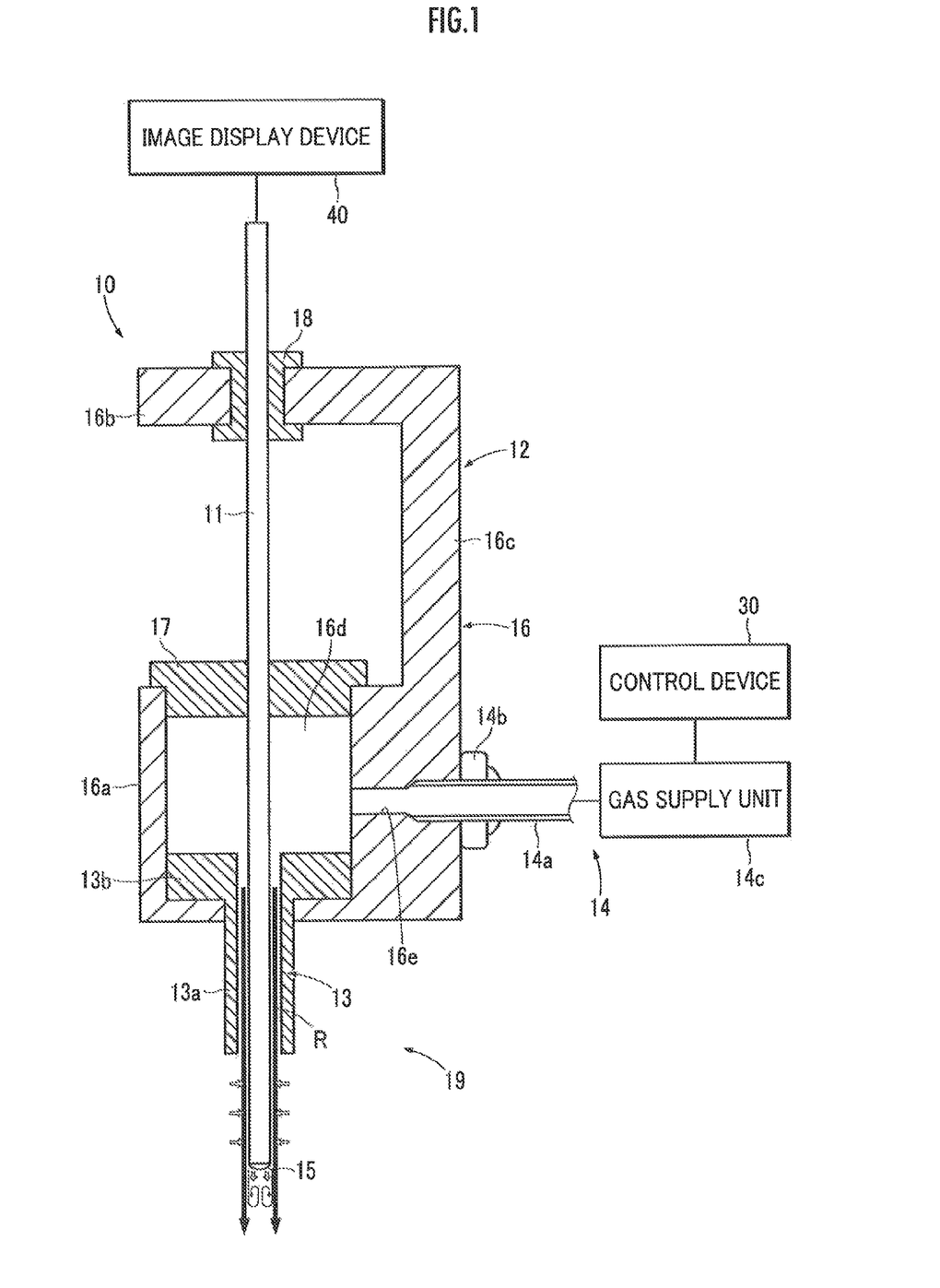
FIG. 1 is a sectional view schematically illustrating a hole inspection device according to an embodiment of the present invention.

The insert shaft 11 is a long and thin stick in overall appearance, a top end portion (lower end portion) in the longitudinal direction thereof (the vertical direction in FIG. 1. Hereinafter, referred to as the vertical direction as well) is inserted into the inspection hole in the inspection. The tip end of the insert shaft 11 is disposed with a wide angle lens 15 such as a fish-eye lens or the like.

In the present embodiment, the insert shaft 11 is configured as an endoscope. Specifically, the insert shaft 11 has a cylindrical outer shell comprised of a hard material such as stainless steel or the like. Although not shown in the drawings, the insert shaft 11 has a lens mechanism including the wide angle lens 15 and a photographing element comprised of CCD, CMOS or the like built inside the top end portion.

However, it is not limited that the insert shaft 11 has the photographing element and the like built therein. For example, it is acceptable that an image of the hole wall surface through the wide angle lens 15 via the lens mechanism built inside the insert shaft 11 or an optical fiber is formed on a photographing surface of a photographing element disposed outside the hole inspection device 10.

Image signals photoelectrically converted from the image of the hole wall surface in the photographing element is transferred via a signal line to an image signal processing unit (not drawn) disposed inside the insert shaft 11 or disposed outside the hole inspection device 10 to generate graphic signals therefrom. The generated graphic signals are output to an image display device 40 disposed outside the hole inspection device 10, thereby, a picture of the hole wall surface is displayed on a display screen of the image display device 40.

The image displayed is inspected visually by an inspector to discover whether or not a defect or the like is present. Although not drawn, it is also acceptable that the generated graphic signals are sent to as graphic analyzing device to automatically determine whether or not a defect or the like is present.

The support bracket 12 is comprised of a bracket main body 16 and two support bushes 17 and 18. The bracket main body 16 is made of a hard material such as stainless steel or the like and is configured to have a first support member 16a and a second support member 16b connected by a connection member 16c to form into an integrated body.

The first support member 16a is positioned at the top end side (lower side) of the bracket main body 16 and is formed inside with a cylindrical space to constitute a gas chamber 16d. The upper surface of the gas chamber 16d is opened. Further, a side wall of the first support member 16a is formed with a gas supply port 16e for supplying gas to the gas chamber 16d. It is desirable that the gas is an inert gas such as nitrogen or air; however, it is not limited thereto.

The first support bush 17 is fixed to the first support member 16a by a nut (not drawn) at the basal end side (upper side) of the first support member 16a to seal the upper surface of the gas chamber 16d. A through hole is formed at the center of the first support bush 17, and the insert shaft 11 is inserted airtightly in the through hole. Thereby, the middle portion of the insert shaft 11 is firmly supported by the first support bush 17.

The second support member 16b is positioned at the basal end side (upper side) of the bracket main body 16 and is formed with a through hole in which the second support bush 18 is installed. A through hole is formed at the center of the second support bush 18, and the insert shaft 11 is inserted in the through hole. Thereby, the basal end portion of the insert shaft 11 is firmly supported by the second support bush 18.

The guide 13 is configured to guide the insert shaft 11 by surrounding the top end portion thereof and meanwhile to guide the injection gas. The guide 13 is made of a material superior in abrasion resistance, for example, an engineering plastic resin such as polyacetal or the like.

The central portion of the guide 13 is formed into a cylindrical through hole in the longitudinal direction (vertical direction) of the insert shaft 11, and the top end portion of the insert shaft 11 is inserted in the through hole. However, the top end of the insert shaft 11 protrudes out of the guide 13. Moreover, the inner circumferential surface of the guide 13 and the outer circumferential surface of the insert shaft 11 are normally noncontact and a gap is formed therebetween. The cylindrical hollow gap extending in the vertical direction forms into a gas injection passage R.

The guide 13 is configured to have a guide main body 13a and a collar member 13b formed into a united body. The guide main body 13a is cylindrical and has an outer diameter roughly the same as the diameter of the through hole formed at the bottom surface of the gas chamber 16d in the first support member 16a. The collar member 13b is an annular plate having an outer diameter roughly the same as the inner diameter of the gas chamber 16d. The collar member 13b is housed in the gas chamber 16d.

According thereto, the guide 13 is restricted unmovable in a direction (lateral direction in FIG. 1) orthogonal to the longitudinal direction (vertical direction) of the insert shaft 11, and the collar member 13b is movable in the vertical direction by sliding within a range in the gas chamber 16d.

The gas supply mechanism 14 is comprised of a hose 14a, a connector (connecting member) 14b for connecting the hose 14a to the gas support port 16e and a gas supply unit 14c including for example a compressor (compression machine), a gas bomb, a control valve and the like. The compressor or the like of the gas supply unit 14c is connected to a control device 30 outside the hole inspection device 10 and is configured to operate according to a control signal from the control device 30 to supply high-pressure gas into the gas chamber 16d.

In the hole inspection device 10 having the above-mentioned configuration, the high-pressure gas supplied from the gas supply unit 14c into the gas chamber 16d is injected via the gas injection passage R into the innermost recess (lower side) of the inspection hole along the outer circumferential surface of the insert shaft 11. Therefore, the gas injection mechanism 19 in the hole inspection device 10 includes the gas injection passage R, the gas chamber 16d, and the gas supply unit 14c.

Hereinafter, a hole inspection method using the hole inspection device 10 according to an embodiment of the present invention will be described.

Firstly, prior to the inspection, the inner side of the inspection hole formed according to a cutting treatment or the like is preliminarily cleaned with water or the like. Thereafter, the top end portion of the insert shaft 11 of the hole inspection device 10 is inserted into the inspection hole automatically or by an operator manually.

At this moment, the high-pressure gas is supplied from the gas supply unit 14c. When the high-pressure gas is supplied into the gas chamber 16d by the gas supply unit 14c, the gas chamber 16d is filled with the high-pressure gas. Thereby, the collar member 13b of the guide 13 is pressed on the bottom surface of the gas chamber 16d by the gas pressure.

Further, the high-pressure gas filled in the gas chamber 16d is injected from the top end of the guide 13 into the innermost recess of the inspection hole along the outer circumferential surface of the insert shaft 11 via the gas injection passage R which is the gap across the entire circumference between the guide 13 and the insert shaft 11 communicating with the gas chamber 16d, as illustrated by the arrows in FIG. 1.

The hole wall surface is photographed by moving the insert shaft 11 gradually toward the innermost recess of the inspection hole if necessary. The photographed image is subjected to an appropriate image process such as a development process or the like, and the image displayed on the image display device 40 is inspected by an inspector visually or by an image analyzing device (not shown) automatically to find whether or not a defect such as a bore or the like is present.

However, it is possible that the hole wall surface after the cleaning treatment still have an adhered substance such as the drops of water used in the cleaning, the chips, the foreign substance or the like which are not removed in the cleaning. If an adhered substance is present on the hole wall surface, it may be detected excessively; thereby, the inspection precision is deteriorated. Furthermore, the inspection hole immediately after the cleaning is at high temperature and high humidity, it is possible that the surface of the wide angle lens 15 will be blurred with the mist. If the lens surface is present with the mist, it is difficult to photograph an image accurately; thereby, the inspection precision is deteriorated.

However, according to the hole inspection method using the hole inspection device 10, while the top end portion of the insert shaft 11 is being inserted into the inspection hole, the gas is injected out from the gas injection passage R to form a laminar flow of gas flowing into the innermost recess of the inspect hole along the whole outer circumferential surface of the top end portion of the insert shaft 11. Accordingly, as illustrated by the blank arrows in FIG. 1, a negative pressure occurs to absorb the adhered substance such as the water drops, the chips, the foreign substance or the like adhered to the hole wall surface to the side of the insert shaft 11 to remove the adhered substance for sure. Thereby, it is possible to improve the inspection precision.

In comparison with an adhered substance cleaning method such as blowing air from outside of the inspection hole, the hole inspection method according to the present invention has equal effects or above in cleaning the adhered substance on the hole wall surface. Thereby, the operation of blowing air into the inspection hole prior to the inspection may be omitted.

As illustrated by the arrows in FIG. 1, by generating an eddy air flux nearby the surface of the wide angle lens 15, a negative pressure occurs to rip the adhered substance away from the lens surface as illustrated by the blank arrows. Thereby, the drops of water, the mist or the like can be removed for sure from the lens surface. Accordingly, even under a high temperature and high humidity environment, it is possible for the wide angle lens 15 to photograph an image clearly, which hereby improves the inspection precision.

Thereby, even though the inspection hole is cleaned with water or the like, it is possible to conduct the inspection (photographing) immediately after the cleaning without the necessity of waiting for the inspection hole to dry. Therefore, it is possible to shorten the inspection time required to finish the inspection.

It is possible to clean the adhered substance adhered on the hole wall surface or n the lens surface at the same time or roughly the same time while the photographing is being conducted. Thereby, it is less possible that a foreign substance or the like flows into the inspection hole after the cleaning and adheres to the hole wall surface or the lens surface before the photographing.

According to Pascal's law, in the gas injection passage R, the high gas pressure acts of the whole outer circumferential surface of the insert shaft 11 equally. Thereby, it is possible to support the top end portion of the insert shaft 11 by the gas pressure without contact at the center of the inner space of the guide 13, enabling the insert shaft 11 to be perfectly supported with the axial center thereof matched with the center of the inner space of the guide 13.

The middle portion and the basal end portion of the insert shaft 11 are supported by the first support bush 17 and the second support bush 18 respectively, and the top end portion of the insert shaft 11 is supported by the gas pressure. Thereby, it is possible to prevent the deviation of the axial center of the insert shaft 11. Even if the deviation of the axial center occurs, it will be automatically corrected; thereby, it is possible to reduce the rattling.

Such effect would be better if the vertical machining precision of the inner wall surface of the gas chamber 16d and the inner wall surface of the guide 13 is perfect. Thus, if the machining precision of the inner wall surfaces is secured sufficiently, there would be no need to use a large-scale hush mechanism which is highly precise but expensive. Thereby, it is possible to miniaturize the support bracket 12, reduce the position deviation of the top end portion of the insert shaft 11, and lower the cost of the device.

For example, when the top end portion of the insert shaft 11 is supported by a conventional bush mechanism, the portion where the bush mechanism is disposed grows in size, which makes it impossible to insert it into a thinner inspection hole. In particular, in the case of inspecting the wall surface of a thin hole to the depth thereof, not a little position deviation occurs at the top end portion of the insert shaft 11. On the contrary, according to the hole inspection device 10 of the present invention, if the inspection hole is in a range for the guide 13 to be inserted, the position deviation nearby the top end portion of the insert shaft 11 can be reduced greatly.

Moreover, by lengthening the guide main body 13a of the guide 13 so as to increase the length of the gas injection passage R, it is possible to inject the gas at a low loss without having a turbulent flow to occur. Thereby, it is possible to stop the lens surface from misting or to clean the adhered substance effectively.

Moreover, the collar member 13b of the guide 13 is pressed downward on the bottom surface of the gas chamber 16d by the gas pressure, thereby, the guide 13 moves upward only when an external force which is greater than the gas pressure is acted thereon upward. Thus, the guide 13 is configured as to move upward easily according to an external force.

Accordingly, even though the guide 13 contacts the wall surface of the hole, the guide 13 moves upward instantly; thereby, it is possible to inhibit the damage to the wall surface of the hole to the minimum.

When an external obstruction, the hole wall surface or the like contacts the guide 13 and exerts a greater external force on the guide 13 in the upward direction, the guide 13 moves upward. Thereby, the collar member 13b of the guide 13 blocks the gas supply port 16e, which stops the gas from being supplied to the gas chamber 16d through the gas supply port 16e from the gas supply unit 14c.

Thus, without disposing a sensor such as a contact sensor or the like in the thin insert shaft 11 or the like but disposing a detection mechanism for detecting the supplied gas pressure outside to the hole inspection device 10, it is possible to detect whether or not a contact with an obstruction is present.

When it is detected that the guide 13 has a contact with an obstruction, by sending an alarm, or by instantly stop the insertion of the hole inspection device 10 when it is being inserted automatically, it is possible to avoid the damage to the hole wall surface or the hole inspection device 10.

If the length of the guide 13 is set so as to minimize the protruding amount of the insert shaft 11, it is possible to further prevent the contact between the insert shaft 11 and the hole wall surface for certain. However, in this case, the outer diameter nearby the top end portion of the hole inspection device 10 is greater, which makes the guide 13 to contact the hole wall surface easier. Therefore, it is desirable to set appropriately the protruding amount of the insert shaft 11 according to a cone angle or the like of the inspection hole.

As mentioned in the above, according to the hole inspection method using the hole inspection device 10, it is possible to obtain three effects as removing the adhered substance away from the hole wall surface or the lens surface, preventing the lens from misting, and supporting stably the insert shaft 11. Thereby, the inspection precision of the hole wall surface is improved.

Figure 2:
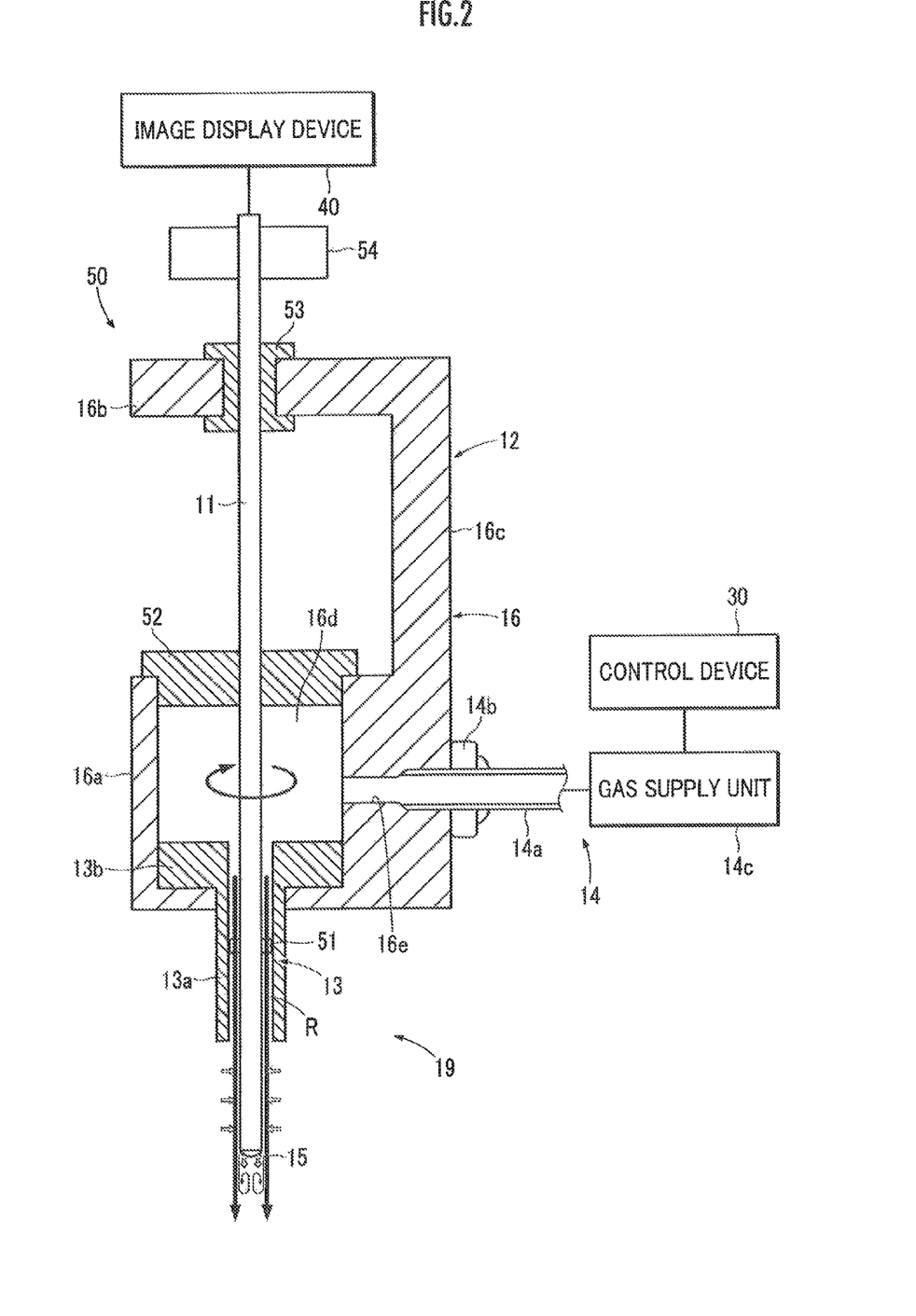
FIG. 2 is a sectional view schematically illustrating a hole inspection device according to another embodiment of the present invention.

Hereinafter, a hole inspection device 50 according to another embodiment of the present invention will be described with reference to FIG. 2. The hole inspection device 50 is similar to the above-mentioned hole inspection device 10; thereby, the description will be carried out only on different configurations and functions. The hole inspection device 50 is configured to have a rotatable insert shaft 11, and is preferably to be used in an ET inspection.

In the ET inspection, an inspection probe is inserted into a hole while being rotated at a constant speed so as to inspect a wall surface of the hole around a lateral surface of the inspection probe. In the ET inspection, according to the electromagnetic induction between the inspection probe and an inspection subject, it is possible to detect a subtle damage and the depth thereof which are beyond recognition in the graph inspection, or to detect a defect such as a bore or the like which is present inside the hole wall surface and which does not appear on the hole wall surface. As the hole inspection device 50 is used in the ET inspection, the insert shaft 11 functions as the inspection probe.

The insert shaft 11 is provided with a turbine blade 51 fixed at the outer circumferential surface thereof opposing to the inner circumferential surface of the guide 13. The insert shaft 11 is rotatably supported by two support bushes 52 and 53 respectively. The basal end portion of the insert shaft 11 is disposed with a rotary encoder 54 for detecting a rotation speed of the insert shaft 11.

In the hole inspection method using the hole inspection device 50, the insert shaft 11 is rotated by the gas flowing in the gas injection passage R. Thereby, if the gas chamber 16d is maintained at a constant pressure, the insert shaft 11 rotates at a constant speed. It is also acceptable to control the rotation speed of the insert shaft 11 by controlling the flow amount of the high-pressure gas supplied to the gas chamber 16d according to a feedback based on the rotation speed detected by the rotary encoder 54.

Similar to the hole inspection method using the hole inspection device 10, it is possible to obtain the same effect according to the hole inspection method using the hole inspection device 50.

In a conventional ET inspection, the inspection probe is rotated by a DC motor or the like serving as a power source. However, in the hole inspection device 50, only by adding the turbine blade 51 without the necessity of disposing the power source such as the DC motor or the like, the insert shaft 11 serving as the inspection probe can be rotated. Thereby, it is possible to simplify the rotating mechanism. Moreover, it is possible to conduct the inspection while removing the adhered substance.

The turbine blade 51 may be adopted in accordance with the pressure or flow amount of the gas flow required to remove the adhered substance so that the insert shaft 11 rotates at the optimum rotation speed constantly. By maintaining the gas chamber 16d at a constant pressure, it is possible to remove the adhered substance with certainty from the hole wall surface or the lens surface while making the insert shaft 11 rotate at a constant speed stably.

The embodiments of the present invention have been described in the above; to however, the present invention is not limited thereto. For example, it is acceptable that the support bracket 12 is not provided with the second support member 16b and the basal end portion of the insert shaft 11 is not supported by the support bush 18. The insert shaft 11, the guide 13 and the gas chamber 16d are described to have a circular shape cross section surface; however, the cross section thereof is not limited to the circular shape, it may be any shape such as a polygonal shape or the like.

DESCRIPTION OF REFERENCE NUMERALS 10, 50: hole inspection device; 11: insert shaft; 12: support bracket (supporter); 13; guide; 13a: guide main body; 13b: collar member; 14: gas supply mechanism; 14a: hose; 14b: connector; 14c: gas supply unit; 15: wide angle lens; 16; bracket main body; 16a: first support member; 16b: second support member; 16c: connection member; 16d: gas chamber; 16e; gas supply port; 17, 52: first support bush; 18, 53: second support bush; 19; gas injection mechanism; 30: control device; 40; image display device; 51: turbine blade; 54: rotary encoder; R: gas infection passage

The invention claimed is:

1. A hole inspection method for inspecting a wall surface of a hole, while an insert shaft disposed with a wide angle lens at a top end thereof is being inserted into the hole to inspect the wall surface of the hole on the basis of an image photographed through the wide angle lens, gas is injected from a bottom side of a top end portion of the insert shaft to flow over the top end portion of the insert shaft in a longitudinal direction of the insert shaft along an outer circumferential surface of the insert shaft toward the top end of the insert shaft, wherein the top end portion of the insert shaft includes the top end of the insert shaft, and the bottom side of the top end portion of the insert shaft is disposed at a position along the top end portion of the insert shaft that is spaced from the top end of the insert shaft, wherein the gas injection mechanism is provided with a guide configured to surround a top end portion of the insert shaft and form a gas injection passage extending in the longitudinal direction of the insert shaft with the outer circumferential surface of the insert shaft, and a gas supply unit configured to supply gas to an inner space of the guide and to inject gas to the gas injection passage.

2. The hole inspection method according to claim 1, wherein the hole is disposed with a fuel injection device.

3. The hole inspection method according to claim 1, wherein gas is injected into a gas injection passage that extends in the longitudinal direction of the insert shaft and is defined between a guide surrounding the top end portion of the insert shaft and the outer circumferential surface of the top end portion of the insert shaft.

4. A hole inspection device for inspecting a wall surface of a hole, comprising:

an insert shaft configured to be inserted into the hole and having a top end portion including a top end of the insert shaft in which a wide angle lens is provided, and a gas injection mechanism configured to inject gas from a bottom side of the top end portion of the insert shaft to flow over the top end portion of the insert shaft in a longitudinal direction of the insert shaft along an outer circumferential surface of the insert shaft toward the top end of the insert shaft, said bottom side of the top end portion of the insert shaft disposed at a position along the top end portion of the insert shaft that is spaced from the top end end of the insert shaft, wherein the gas injection mechanism is provided with a guide configured to surround a top end portion of the insert shaft and form a gas injection passage extending in the longitudinal direction of the insert shaft with the outer circumferential surface of the insert shaft, and a gas supply unit configured to supply gas to an inner space of the guide and to inject gas to the gas injection passage.

5. The hole inspection device according to claim 4 is further provided with a supporter having a gas chamber which is supplied with gas from the gas supply unit, houses a collar member disposed at a basal end of the guide, and communicates the inner space of the guide, wherein the insert shaft is disposed so as to insert through the guide and the gas chamber in the longitudinal direction and a basal end portion thereof is supported by the supporter.

6. The hole inspection device according to claim 4, wherein the hole is disposed with a fuel injection device.

7. The hole inspection device according to claim 4, wherein the hole is disposed with a fuel injection device.

8. The hole inspection device according to claim 5, wherein the hole is disposed with a fuel injection device.

9. A hole inspection device for inspecting a wall surface of a hole, comprising:

an insert shaft configured to be inserted into the hole and having a top end portion including a top end of the insert shaft in which a wide angle lens is provided, and a gas injection mechanism comprising a guide configured to surround a top end portion of the insert shaft and form a gas injection passage extending in the longitudinal direction of the insert shaft with the outer circumferential surface of the insert shaft, and a gas supply unit configured to supply gas to an inner space of the guide, wherein the gas injection mechanism is configured to inject gas from a bottom side of the top end portion of the insert shaft to flow over the top end portion of the insert shaft in a longitudinal direction of the insert shaft along an outer circumferential surface of the top end portion of the insert shaft protruding from the guide toward the top end of the insert shaft, said bottom side of the top end portion of the insert shaft disposed at a position along the top end portion of the insert shaft that is spaced from the top end of the insert shaft.

* * * * *

UNITED STATES PATENT AND TRADEMARK OFFICE
CERTIFICATE OF CORRECTION

PATENT NO. : 9,078,558 B2
APPLICATION NO. : 13/565694
DATED : July 14, 2015
INVENTOR(S) : Ishizuka et al.

It is certified that error appears in the above-identified patent and that said Letters Patent is hereby corrected as shown below:

Delete the title page and substitute therefor the attached title page.

In the claims

Column 9, Line 18, (Claim 1, Line 17), delete "a top end" and insert --the top end--.

Column 10, Line 3, (Claim 4, Line 16), delete "a top end" and insert --the top end--.

Column 10, Line 20, (Claim 7), delete Claim 7 in its entirety.

Column 10, line 22, "8." should be changed to --7.--.

Column 10, line 24, "9." should be changed to --8.--.

Signed and Sealed this
Ninth Day of August, 2016

Michelle K. Lee
*Director of the United States Patent and Trademark Office*

(12) United States Patent
Ishizuka et al.

(10) Patent No.: US 9,078,558 B2
(45) Date of Patent: Jul. 14, 2015

(54) HOLE INSPECTION METHOD AND HOLE INSPECTION DEVICE

(75) Inventors: Yasutaka Ishizuka, Tochigi (JP); Satoshi Oikawa, Tochigi (JP); Michiaki Ohkubo, Tochigi (JP); Masaichi Ohno, Tochigi (JP)

(73) Assignee: HONDA MOTOR CO., LTD., Tokyo (JP)

(*) Notice: Subject to any disclaimer, the term of this patent is extended or adjusted under 35 U.S.C. 154(b) by 415 days.

(21) Appl. No.: 13/565,694

(22) Filed: Aug. 2, 2012

(65) Prior Publication Data
US 2013/0093876 A1  Apr. 18, 2013

(30) Foreign Application Priority Data
Oct. 13, 2011  (JP) ................... 2011-225947

(51) Int. Cl.
H04N 7/18       (2006.01)
A61B 1/00      (2006.01)
A61B 1/12      (2006.01)
G02B 23/24    (2006.01)

(52) U.S. Cl.
CPC ............ *A61B 1/00* (2013.01); *A61B 1/0008* (2013.01); *A61B 1/00064* (2013.01); *A61B 1/00071* (2013.01); *A61B 1/00091* (2013.01); *A61B 1/12* (2013.01); *G02B 23/2492* (2013.01)

(58) Field of Classification Search
CPC ........ H04N 7/18; H04N 5/91; H04N 5/225; H04N 5/232; H04N 5/23222; H04N 9/045; H04N 2005/2255

USPC ............. 348/82, 84, 85; 73/152.58; 367/35
See application file for complete search history.

(56) References Cited

U.S. PATENT DOCUMENTS

| 4,883,355 | A |   | 11/1989 | Saghatchi et al. |
| 4,938,060 | A | * | 7/1990  | Sizer et al. ............... 73/152.58 |
| 5,191,173 | A | * | 3/1993  | Sizer et al. ............... 174/105 R |
| 2005/0281520 | A1 |   | 12/2005 | Kehoskie et al. |
| 2010/0317922 | A1 |   | 12/2010 | Kumai |

FOREIGN PATENT DOCUMENTS

| EP | 0 242 428 A2 | 10/1987 |
| JP | 58-62612 A | 4/1983 |
| JP | 10-76825 A | 3/1989 |
| JP | 1-130119 A | 5/1989 |
| JP | 1-229218 A | 9/1989 |
| JP | 1-239219 A | 9/1989 |
| JP | 1-255821 A | 10/1989 |

(Continued)

*Primary Examiner* — Trang U Tran
(74) *Attorney, Agent, or Firm* — Rankin, Hill & Clark LLP (57) ABSTRACT

While an insert shaft (11) disposed with a wide angle lens (15) at a top end thereof is being inserted into a hole to inspect a wall surface of the hole on the basis of an image photographed through the wide angle lens (15), gas is injected into the innermost recess of the hole along the outer circumferential surface of the insert shaft (11) by a gas injection mechanism (19). The gas injection mechanism (19) is provided with a guide (13) configured to surround a top end portion of the insert shaft (11) and form a gas injection passage (R) extending in the longitudinal direction of the insert shaft (11) between the inner circumferential surface of the guide (13) and the outer circumferential surface of the insert shaft (11), and a gas supply unit (14c) configured to supply gas to an inner space of the guide (13).

8 Claims, 2 Drawing Sheets